United States Patent
Wang et al.

(10) Patent No.: US 11,266,716 B2
(45) Date of Patent: Mar. 8, 2022

(54) USE OF DERMCIDIN IN STERILE INFLAMMATORY CONDITIONS

(71) Applicant: THE FEINSTEIN INSTITUTES FOR MEDICAL RESEARCH, Manhasset, NY (US)

(72) Inventors: Ping Wang, Roslyn, NY (US); Haichao Wang, Edison, NJ (US)

(73) Assignee: THE FEINSTEIN INSTITUTES FOR MEDICAL RESEARCH, Manhasset, NY (US)

(*) Notice: Subject to any disclaimer, the term of this patent is extended or adjusted under 35 U.S.C. 154(b) by 272 days.

(21) Appl. No.: 15/769,880

(22) PCT Filed: Oct. 21, 2016

(86) PCT No.: PCT/US2016/058027
§ 371 (c)(1),
(2) Date: Apr. 20, 2018

(87) PCT Pub. No.: WO2017/070421
PCT Pub. Date: Apr. 27, 2017

(65) Prior Publication Data
US 2019/0030124 A1    Jan. 31, 2019

Related U.S. Application Data

(60) Provisional application No. 62/244,779, filed on Oct. 22, 2015.

(51) Int. Cl.
| | |
|---|---|
| *A61K 38/17* | (2006.01) |
| *A61K 38/16* | (2006.01) |
| *A61K 47/54* | (2017.01) |
| *A61K 47/60* | (2017.01) |
| *A61P 29/00* | (2006.01) |
| *A01N 1/02* | (2006.01) |
| *A61K 9/00* | (2006.01) |

(52) U.S. Cl.
CPC ........ *A61K 38/1729* (2013.01); *A01N 1/0215* (2013.01); *A61K 9/0014* (2013.01); *A61K 9/0019* (2013.01); *A61K 38/16* (2013.01); *A61K 47/549* (2017.08); *A61K 47/60* (2017.08); *A61P 29/00* (2018.01)

(58) Field of Classification Search
CPC .. A01N 1/0215; A61K 38/16; A61K 38/1729; A61K 47/549; A61K 47/60; A61K 9/0014; A61K 9/0019; A61P 29/00; H01H 23/00; H01H 61/02
See application file for complete search history.

(56) References Cited

U.S. PATENT DOCUMENTS

| | | | |
|---|---|---|---|
| 2007/0009880 A1 | 1/2007 | Toledo et al. | |
| 2007/0015711 A1* | 1/2007 | Szeto ............ | A61K 38/07 514/1.4 |
| 2009/0221542 A1 | 3/2009 | Wang et al. | |
| 2009/0149673 A1 | 6/2009 | Zhang et al. | |
| 2009/0175797 A1 | 7/2009 | Warren et al. | |
| 2013/0143828 A1 | 6/2013 | Moteni | |

OTHER PUBLICATIONS

Cunningham et al. Identification of the Human cDNA for New Survival/Evasion Peptide (DSEP): Studies in Vitro and in Vivo of Overexpression by Neural Cells. Experimental Neurology, vol. 177, pp. 32-39 (Year: 2002).*
PCT International Search Report and Written Opinion dated Feb. 21, 2017 in connection with PCT International Application No. PCT/US2016/58027, 11 pages.

* cited by examiner

*Primary Examiner* — Marcela M Cordero Garcia
(74) *Attorney, Agent, or Firm* — Amster, Rothstein & Ebenstein LLP

(57) ABSTRACT

A method of treating a sterile inflammatory condition in a subject using an isolated dermcidin peptide or an active fragment thereof of or an active analog thereof is provided. Also provided is a method of inhibiting organ transplantation-associated is chemia/reperfusion and/or organ transplantation-associated inflammation.

2 Claims, 7 Drawing Sheets
Specification includes a Sequence Listing.

A Dermcidin precursor (a.a. 20-110) and proteolytic peptides.

```
20                                            63                                              110
YDPEAASAPGSGNPCHEASAAQKENAGEDPGLARQAPKPRKQRSS LLEKGLDGAKKAVGGLGKLGKDAVEDLESVGKGAVHDVKDVLDSVL

DCD-1L  (63-110)                              SSLLEKGLDGAKKAVGGLGKLGKDAVEDLESVGKGAVHDVKDVLDSVL
DCD-1   (63-109)                              SSLLEKGLDGAKKAVGGLGKLGKDAVEDLESVGKGAVHDVKDVLDSV
SSL25   (63-87)                               SSLLEKGLDGAKKAVGGLGKLGKDA
```

Survival (anti-oxidant)    Anti-microbial

B SDS-PAGE (Coomassie blue)

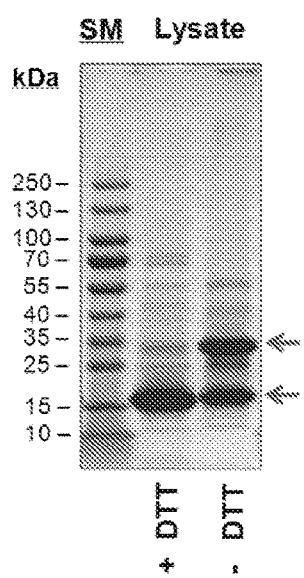
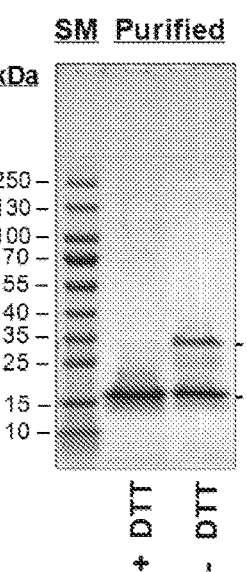

C Western blot (Abcam 175519)

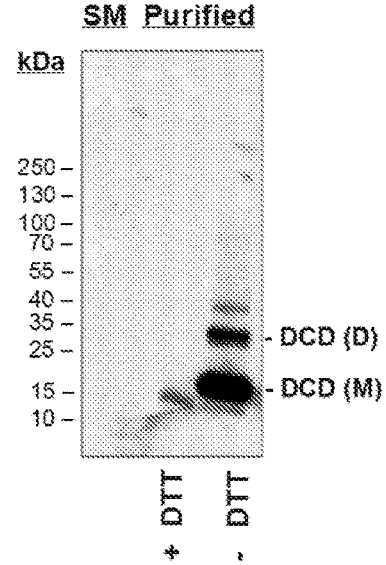

Fig. 1

USE OF DERMCIDIN IN STERILE INFLAMMATORY CONDITIONS

CROSS-REFERENCE TO RELATED APPLICATIONS

This application is a U.S. national stage entry under 35 U.S.C. § 371 of PCT International Patent Application No. PCT/US2016/058027, filed Oct. 21, 2016, which claims the benefit of U.S. Provisional Patent Application No. 62/244,779, filed Oct. 22, 2015, the contents of which are incorporated herein by reference into the subject application.

STATEMENT OF GOVERNMENT SUPPORT

This invention was made with government support under grant nos. AT005076, GM063075, GM053008, and GM076179 awarded by the National Institutes of Health. The government has certain rights in the invention.

BACKGROUND OF THE INVENTION

Throughout this application various patents and other publications are referred to in parenthesis. Full citations for the references may be found at the end of the specification. The disclosures of these patents and publications are hereby incorporated by reference in their entirety into the subject application to more fully describe the art to which the subject invention pertains.

Despite advances in medicine, conditions in which inflammatory responses result in complications, injury or death continue to be a problem area. This is true even in the case of sterile inflammatory responses.

The present invention addresses the need for a new anti-inflammatory treatments and compositions.

SUMMARY OF THE INVENTION

Provided is a method for treating a sterile inflammatory condition in a subject comprising administering to the subject an amount of an isolated dermcidin peptide, or an active fragment thereof or an active analog thereof, effective to treat a sterile inflammatory condition.

Also provided is a method of inhibiting organ transplantation-associated ischemia/reperfusion and/or organ transplantation-associated inflammation in a recipient subject comprising storing and/or rinsing the organ to be transplanted in a solution comprising an amount of an isolated dermcidin peptide, or an active fragment thereof or an active analog thereof, effective to inhibit organ transplantation-associated ischemia/reperfusion and/or organ transplantation-associated inflammation in a recipient subject.

Also provided is a method of treating an inflammatory condition in a subject comprising administering to the subject an amount of an isolated dermcidin peptide, or an active fragment thereof or an active analog thereof, effective to treat an inflammatory condition.

Additional objects of the invention will be apparent from the description which follows.

BRIEF DESCRIPTION OF THE DRAWINGS

FIG. 1A-1C. Expression and purification of recombinant dermcidin. A). Amino acid sequence of dermcidin precursor and various proteolytic peptides. From top to bottom SEQ ID NOS:1, 7, 8, and 6, respectively). DCD-1L is a 48 amino acid peptide corresponding to the C-terminal of the full length of dermcidin precursor. B). Expression and purification of recombinant histidine-tag dermcidin precursor (20-110) (DCD). Recombinant dermcidin corresponding to residue 20-110 amino acid with an N-terminal histidine tag was expressed in $E.$ $coli$ BL21 (DE3) pLysS cells (Panel B, left gel), and purified by histidine-affinity chromatography (Panel B, right gel) and Triton X-114 extraction to remove contaminating endotoxins. Note that recombinant dermcidin migrated on SDS-PAGE gel as a 12-14 kDa monomer (DCD M) in the presence of a reducing agent (dithiothreitol, DTT), but migrated as both a monomer and 24-28 kDa dimer (24-28 kDa) in the absence of DTT, suggesting possible cross-linking between dimers through disulfide bonds. C). Confirmation of the identify of recombinant protein by Western blotting analysis using dermcidin-specific antibodies.

DETAILED DESCRIPTION OF THE INVENTION

Figure 2:
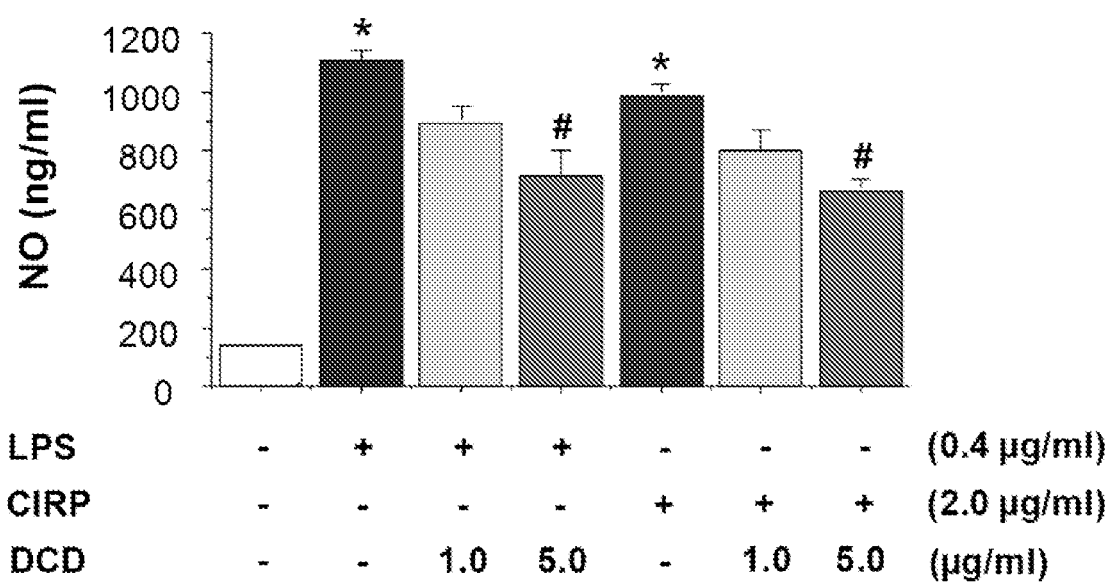
FIG. 2. Dermcidin dose-dependently attenuated LPS- and CIRP-induced NO release by murine macrophages. Murine macrophages were stimulated with LPS or CIRP alone or in the presence of recombinant dermcidin (DCD) for 16 hours, and extracellular levels of nitric oxide (NO) were determined by the Griess Reagent. *, $P<0.05$ versus "−control"; #, $P<0.05$ versus "+LPS", or "+CIRP" alone.

A method is provided for treating a sterile inflammatory condition in a subject comprising administering to the subject an amount of an isolated dermcidin peptide, or an active fragment thereof of or an active analog thereof, effective to treat a sterile inflammatory condition.

In an embodiment, the sterile inflammatory condition is caused by or associated with ischemia-reperfusion in an organ in the subject. In an embodiment, the sterile inflammatory condition is caused by or associated with ischemia-reperfusion in a gastrointestinal tract, liver, lung, kidney, heart, brain or crushed limb of the subject.

Also provided is a method of inhibiting organ transplantation-associated ischemia/reperfusion and/or organ transplantation-associated inflammation in a recipient subject comprising storing and/or rinsing the organ to be transplanted in a solution comprising an amount of an isolated dermcidin peptide, or an active fragment thereof or an active analog thereof, effective to inhibit organ transplantation-associated ischemia/reperfusion and/or organ transplantation-associated inflammation in a recipient subject. In an embodiment, the isolated dermcidin peptide, or an active fragment thereof or an active analog thereof, is used as an adjuvant in an organ transplantation storage and/or organ transplantation rinse solution. In an embodiment, the organ is a kidney, liver, heart, or lung. The organ transplantation storage and/or organ transplantation in an embodiment is a known and/or clinically used organ transplantation storage and/or organ transplantation.

In an embodiment of the methods, the isolated dermcidin peptide is administered to the subject, or used in the storing and/or rinsing, respectively. In an embodiment of the methods, the isolated dermcidin peptide has the sequence of full-length human dermcidin without its signal sequence.

In an embodiment of the methods, the active analog of dermcidin is administered to the subject, or used in the storing and/or rinsing, respectively. In an embodiment of the methods, the active analog of dermcidin has a Cysteine-Serine substitution that prevents dimerization via disulfide bonds between cysteine 34 of two dermcidin peptides. In an embodiment of the methods, the active fragment of dermcidin is administered to the subject, or used in the storing and/or rinsing, respectively.

In an embodiment, a pharmaceutically acceptable salt of dermcidin peptide or of a dermcidin fragment or analog is used.

In an embodiment, the dermcidin peptide has the sequence: YDPEAASAPGSGNPCHEASAAQKENAGE-DPGLARQAPKPRKQRSSLLEKGLDGAKKAVGGLG-KLGKDAVEDLESVGKGAVHDVKDVLDSVL (SEQ ID NO:1). In an embodiment, the "cysteine 34" as referred to herein is the underlined C in SEQ ID NO: 1. In an embodiment, the dermcidin active fragment has one of the following sequences:

```
                                          (SEQ ID NO: 2)
ESVGKGAVHDVKDVLDS;

(SEQ ID NO: 3)
LLGDFFRKSKEKIGKEFKRIVQRIKDFLRNLVPRTES;

(SEQ ID NO: 4)
LEKGLDGAKKAVGGLGKLGKDAVE;

(SEQ ID NO: 5)
SSLLEKGLDGAKKAVGGLGKLGKDAVEDL;
or (SEQ ID NO: 6)
SSLLEKGLDGAKKAVGGLGKLGKDA.
```

In an embodiment, the dermcidin fragment is DCD-1L, DCD-1 or SSL25 as shown in FIG. 1A.

In an embodiment of the methods, the peptide, analog or fragment is modified to improve its plasma half-life. In an embodiment of the methods, the peptide, analog or fragment is modified by being PEGylated or mannosylated.

In an embodiment of the methods wherein administration is employed, the amount of an isolated dermcidin peptide or an active fragment thereof or an active analog thereof is administered by intra-arterial, intravenous, intraventricular, or topical administration. Other routes of medicament administration known in the art may also be used.

Also provided is a method of treating an inflammatory condition in a subject comprising administering to the subject an amount of an isolated dermcidin peptide, or an active fragment thereof or an active analog thereof, effective to treat an inflammatory condition.

In an embodiment, the inflammatory condition is sepsis, septicemia or endotoxemia.

In an embodiment, the inflammatory condition is sepsis. In an embodiment, the isolated dermcidin peptide, or an active fragment thereof or an active analog thereof is administered intraperitoneally.

In an embodiment, the inflammatory condition is septicemia. In an embodiment, the isolated dermcidin peptide, or an active fragment thereof or an active analog thereof is administered intravascularly.

In an embodiment, the inflammatory condition is endotoxemia.

In an embodiment of the methods, the active fragment of dermcidin is administered or used. In an embodiment of the methods, the peptide, analog or fragment is modified to improve its plasma half-life. In an embodiment of the methods, the peptide, analog or fragment is modified with PEGylation or mannosylation. In an embodiment of the methods, the active analog of dermcidin is administered or used. In an embodiment of the methods, the isolated dermcidin peptide is administered or used. In an embodiment of the methods, the isolated dermcidin peptide has the sequence of full-length human dermcidin without its signal sequence. In an embodiment of the methods, the active analog of dermcidin has a Cysteine→Serine substitution that prevents dimerization via disulfide bonds between cysteine 34 of two dermcidin peptides.

In an embodiment of the methods, the subject is a human subject.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Introduction

Cohabitating with various microbes over millions of years, animals have developed multiple strategies to deal with microbial infections. The epidermal barriers of the skin serve as the first layer of defense by limiting the physical access of many pathogens to the blood circulation. In addition, sweat glands secrete a wide array of antimicrobial peptides, which restrain the growth of various microbes on the skin. For instance, during rigorous physical exercise, an antimicrobial peptide, called dermcidin, is secreted by the sweat glands onto the epidermal surface of the skin (1). It has been proposed that dermcidin can be activated in salty and slightly acidic sweat to form channels that can possibly perforate microbe membranes, allowing water and $Zn^{+2}$ ions in sweat to gush across the cell membrane, killing the microbe (2, 3). Despite its capacity in binding to various bacterial strains, dermcidin has not yet been reproducibly shown to permeabilize bacterial membranes (4), calling for further investigation in this arena. Nevertheless, at body sites in frequent contact with pathogenic microbes, a higher amount of dermcidin peptide is detected in sweat (5), supporting the essential role of sweat in the regulation of skin microbial flora.

Prior to the disclosure herein, however, to applicants' knowledge it was not known that dermcidin also has mammalian immune system-modulating properties and anti-inflammatory properties.

As the first line of defense against microbial infection, monocytes continuously patrol the body in search of invading pathogens or damaged tissues, and can immediately infiltrate the infected/injured tissue upon the detection of microbial products or host-derived chemotactic factors. Once reaching extravascular tissues, these monocytes are differentiated into tissue-specific resident macrophages, which ingest and eliminate invading pathogens in conjunction with other phagocytes (e.g., neutrophils). Additionally, macrophages/monocytes are equipped with pattern recognition receptors [such as the Toll-like receptors (TLRs) TLR2, TLR3, TLR4, and TLR9] (7) for various pathogen-associated molecular patterns (PAMPs, such as bacterial peptidoglycan, double-stranded RNA, endotoxin, and CpG-DNA) (8). The engagement of various PAMPs with respective receptors triggers release of various proinflammatory mediators such as high mobility group box 1 (HMGB1) (9), cold-inducible RNA-binding protein (CIRP) (10, 11) as well as nitric oxide (NO) (12). In addition to active secretion, HMGB1 can also be passively released from damaged cells (13) following ischemia/reperfusion (14), trauma (15), or toxemia (16), thereby serving as a damage-associated molecular pattern molecule (DAMP). Thus, infection and injury converge on a common process, inflammation (17), which is orchestrated by HMGB1 and other proinflammatory mediators (e.g., CIRP) derived from activated immune cells and damaged tissues (10). If dysregulated, the excessive production of these proinflammatory mediators (e.g., HMGB1, NO, and CIRP) (9, 10, 12, 18), individually or in combination, contribute to the pathogenesis of inflammatory diseases.

Herein is provided evidence that dermcidin exhibits immune-modulating properties in response to PAMP or DAMP.

Dermcidin is expressed in sweat glands, and in the absence of an inflammatory stimulus, is constitutively secreted as a full-length protein (1). This full length precursor can be further processed by unknown proteases in human sweat, to form several shorter peptides that exhibit anti-oxidant and antimicrobial activities (FIG. 1A). For instance, the N-terminal peptide (residue 20-62) has been shown to protect various types of cells against oxidative or hypoxic stresses (25-27). On the other hand, many C-terminal peptides exhibit anti-microbial properties against *S. aureus*, *E. coli*, *E. faecalis*, and *C. albicans* (1). In addition to sweat glands, innate immune cells (e.g., monocytes) also express dermcidin in response to viral infection (28). Furthermore, the full-length dermcidin precursor (residue 22-110) also exhibits bacterial killing activities towards *S. aureus*, *E. coli*, and *P. acnes* (29). A C-terminal peptide, DCD-1L, has been shown to activate keratinocytes to produce cytokines (e.g., TNF) and chemokines (e.g., IL-8/CXCL8, CXCL10, and CCL20) (30). Herein it is disclosed that dermcidin precursor divergently modulated PAMP- and DAMP-induced production of TNF, NO, and chemokines by innate immune cells.

Figure 3:
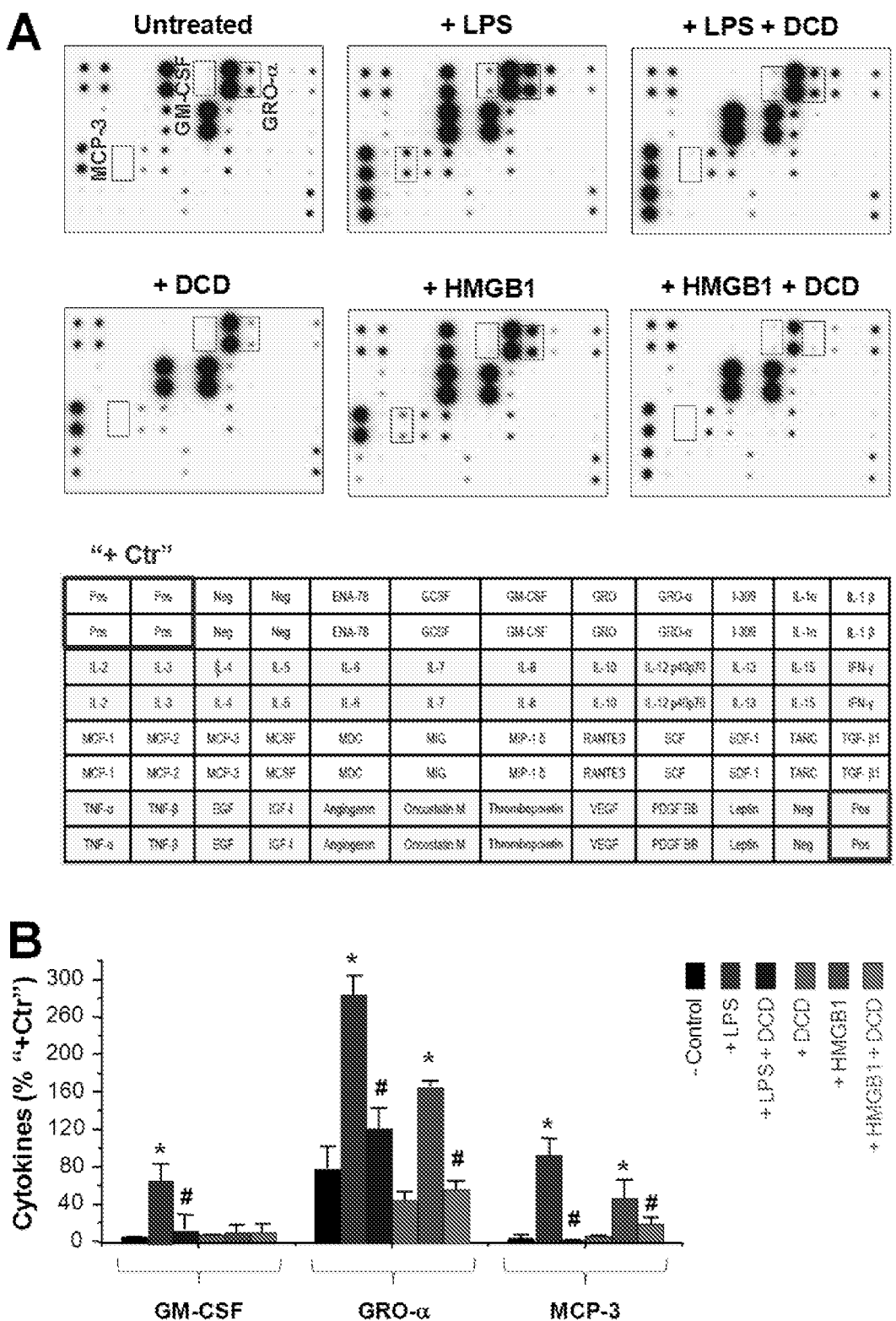
FIG. 3A-3B. Dermcidin modulated LPS- and HMGB1-induced chemokine release by human monocytes. Human peripheral mononuclear cells (huPBMCs) were stimulated with LPS (0.8 µg/ml) or HMGB1 (4.0 µg/ml) alone, or in the presence of DCD (1.0 µg/ml) for 16 hours, and extracellular levels of cytokines and chemokines were determined by Cytokine Antibody Arrays (Panel A, B). A, Representative cytokine antibody arrays. The name of the cytokines and positive controls ("Pos", or "+Ctrl") were labeled in the table below. B, Relative cytokine levels. The relative cytokine levels were estimated by measuring the intensity of corresponding signal, and expressed as mean±SEM [% of positive controls ("+Ctrl") of respective arrays] of two independent experiments. *, $P<0.05$ versus "untreated"; #, $P<0.05$ versus "+LPS" or "+HMGB1" alone.

Recombinant human dermcidin protein was generated in *E. coli*, and purified to homogeneity in the absence or presence of a reducing agent (DTT, FIG. 1B). Although migrating at a slightly lower rate than the predicted molecular weight, the identity of this recombinant dermcidin was confirmed by Western blotting analysis using a commercially available antibody (FIG. 1C). This is consistent with a recent report that recombinant histidine tag-DCD migrated as a 15-16 kDa band on SDS-PAGE gel, even though its molecular weight was determined to be ~9.25 kDa by mass spectrometry (29). Using purified dermcidin, we then tested its immune-modulating properties using macrophage and monocyte cultures. In response to PAMPs (e.g., bacterial endotoxin, LPS) or endogenous cytokines (e.g., CIRP), macrophages released large amounts of nitric oxide (NO, FIG. 2). However, dermcidin (DCD) dose-dependently and significantly attenuated both LPS- and CIRP-induced NO release (FIG. 2). Although activated monocytes cannot produce NO, they do produce various proinflammatory cytokines or chemokines. Human monocytes were stimulated with PAMPs (e.g., LPS) or DAMPs (e.g., HMGB1), in the absence or presence of DCD. The, relative levels of various cytokines/chemokines in the monocyte-conditioned culture medium were measured using Cytokine Antibody Arrays (FIG. 3). As shown in FIG. 3, both LPS and HMGB1 elevated the relative levels of several chemokines such as GRO-α and MCP-3. Similarly, dermcidin effectively inhibited LPS- and HMGB1-induced release of GRO-α and MCP-3 from human monocyte cultures (FIG. 3). Despite the inhibitory effects on the above chemokines, dermcidin slightly stimulated TNF secretion, an early proinflammatory cytokine that propagates protective innate immune response against microbial infection. In agreement with the stability of dermcidin's anti-bacterial properties over a broad pH range and salt concentrations (1), it was found that dermcidin's immune-modulating properties were also relatively stable. Although dermcidin tended to form dimers in the absence of reducing agents (FIG. 1B), its immune modulating properties remained unaltered (data not shown), indicating the relative stability of dermcidin's biological activities in vitro.

In animal models of peritoneal microbial infection induced by surgical perforation of the cecum, a technique known as cecal ligation and puncture (CLP) (31), neutralizing antibodies against TNF worsens the outcome (32), supporting a beneficial role of TNF in the innate immunity against bacterial infection. Although appropriate inflammatory responses might be needed for the innate immunity against microbial infection, excessive recruitment of leukocyte to infection or injury sites might be harmful to the host. As a critical element of the innate immune response, leukocyte recruitment is governed by chemotactic functions of bacterial products and chemokines (such as GRO-α and MCP-3) (33). The dermcidin-mediated suppression of both PAMP- and DAMP-induced chemokines (such as GRO-α and MCP-3) might attenuate leukocyte recruitment to the infection and injury site, and likely prevent excessive inflammatory responses to infection or injury.

Although many anti-inflammatory agents have failed to improve outcomes of many inflammatory diseases (such as sepsis), the investigation of pathogenic cytokines in animal models of diseases has led to the development of successful cytokine-targeting therapeutic strategies (e.g., anti-TNF antibody, infliximab) for autoimmune diseases such as rheumatoid arthritis (34, 35). The dual anti-bacterial (29) and anti-inflammatory (FIG. 2 and FIG. 3) properties may distinguish dermcidin from previously tested anti-inflammatory agents, positioning it as a unique experimental agent for preclinical testing using various animal models of inflammatory diseases. Given the complex and redundant roles of various cytokines and chemokines in various inflammatory diseases, it is now particularly important to test the hypothesis that dermcidin may occupy an important role in the regulation of local or systemic inflammation in preclinical animal models. For instance, injection of bacterial endotoxin directly into the skin (e.g., footpad, subcutaneously) provides a murine model of local inflammation and edema. It is interesting to determine whether local co-administration of dermcidin attenuates paw edema at various time points after endotoxin challenge. Additionally, systemic inflammation can be induced in animals by infusion of bacterial endotoxin such as LPS (31), or surgical perforation of the cecum, a technique aforementioned as CLP (31). Systemic administration (intraperitoneally or intravenously) of dermcidin may confer a dose-dependent protection against lethal endotoxemia or CLP-induced bacteremia.

Figures 4A, 4B:
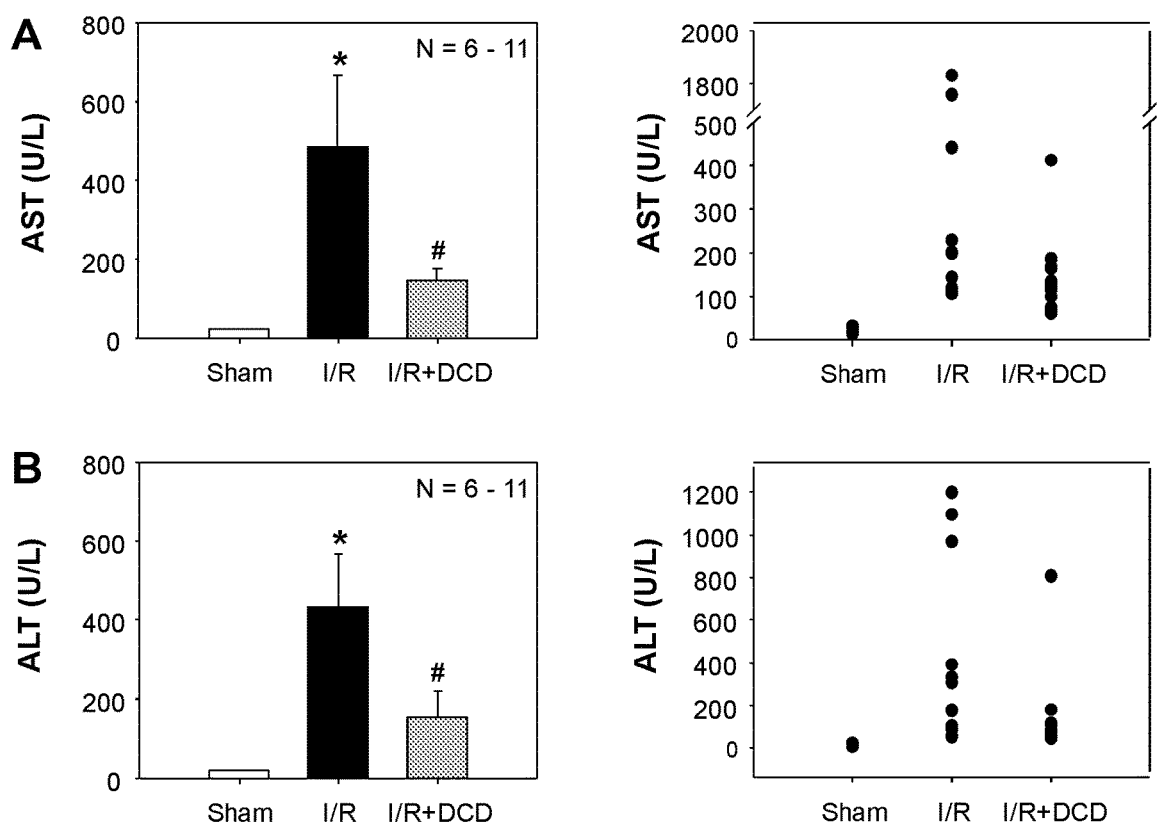
FIG. 4A-4B. Intravenous administration of dermcidin conferred protection against hepatic ischemia/reperfusion (I/R) injury. Male C57BL/6 mice (20-25 g) were subjected to hepatic ischemia/reperfusion by temporal clamping the hepatic artery and portal vein for 60 minutes, which typically produced ischemia in 70% of the liver. At the beginning of the reperfusion, 0.2 ml saline or recombinant dermcidin solution ("DCD", 5.0 mg/kg BW) was injected via the internal jugular vein. At 24 h after the onset of ischemia, animals were euthanized to harvest blood to measure serum levels of hepatic injury markers such as alanine aminotransferase (ALT) (4A) and aspartate aminotransferase (AST) (4B) using commercial kits. Note that dermcidin promoted significant protection against I/R injury. *, $P<0.05$ versus sham control; #, $P<0.05$ versus saline group ("I/R").

In further experiments, intravenous administration of dermcidin conferred protection against hepatic ischemia/reperfusion (I/R) injury. Male C57BL/6 mice (20-25 g) were subjected to hepatic ischemia/reperfusion by temporal clamping the hepatic artery and portal vein for 60 minutes, which typically produced ischemia in 70% of the liver. At the beginning of the reperfusion, 0.2 ml saline or recombinant dermcidin solution ("DCD", 5.0 mg/kg BW) was injected via the internal jugular vein. At 24 h after the onset of ischemia, animals were euthanized to harvest blood to measure serum levels of hepatic injury markers such as alanine aminotransferase (ALT) and aspartate aminotransferase (AST) using commercial kits. Dermcidin promoted significant protection against I/R injury. (see FIG. 4)

Figure 5:
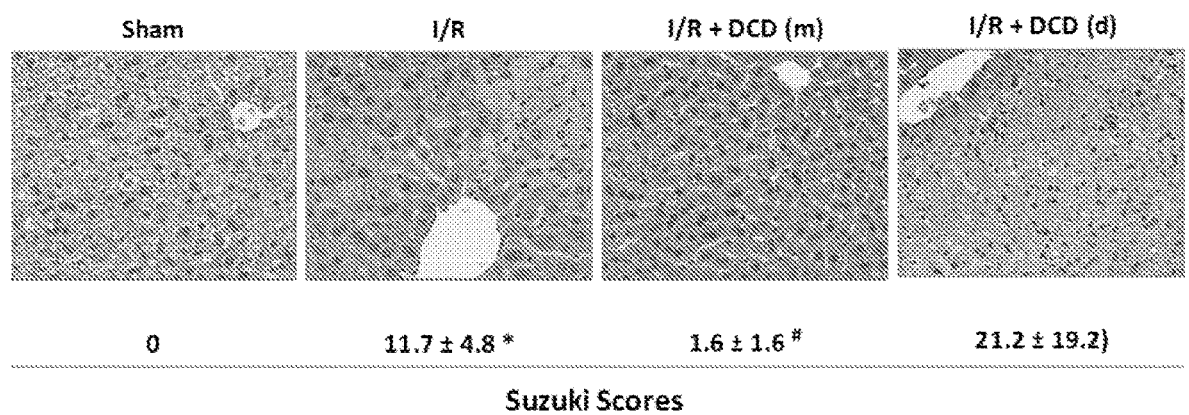
FIG. 5. DCD monomer protects against hepatic ischemic/reperfusion injury. Representative liver histology at 24 h post the onset of reperfusion. Note a normal liver parenchyma architecture in the "Sham" control, but hepatic necrosis in the "I/R". Unlike the DCD dimer-treated group ["I/R+DCD (d)"], the DCD monomer-treated group ["I/R+DCD (m)"] exhibited a well-preserved tissue structure. Liver injury was also assessed histologically using the Suzuki liver injury scores, and expressed as means±S.E. of 3-6 animals per group. *$P<0.05$ vs. sham; #$P<0.05$ vs. "I/R" group.

The DCD monomer protects against hepatic ischemic/reperfusion injury, as shown in FIG. 5. A representative liver histology at 24 h post the onset of reperfusion is shown, note a normal liver parenchyma architecture in the "Sham" control, and hepatic necrosis in the "I/R". Unlike the DCD dimer-treated group ["I/R+DCD (d)"], the DCD monomer-treated group ["I/R+DCD (m)"] exhibited a well-preserved tissue structure. Liver injury was also assessed histologically using the Suzuki liver injury scores, and expressed as means±S.E. of 3-6 animals per group. *P<0.05 vs. sham; #P<0.05 vs. "I/R" group.

Figures 6A, 6B:
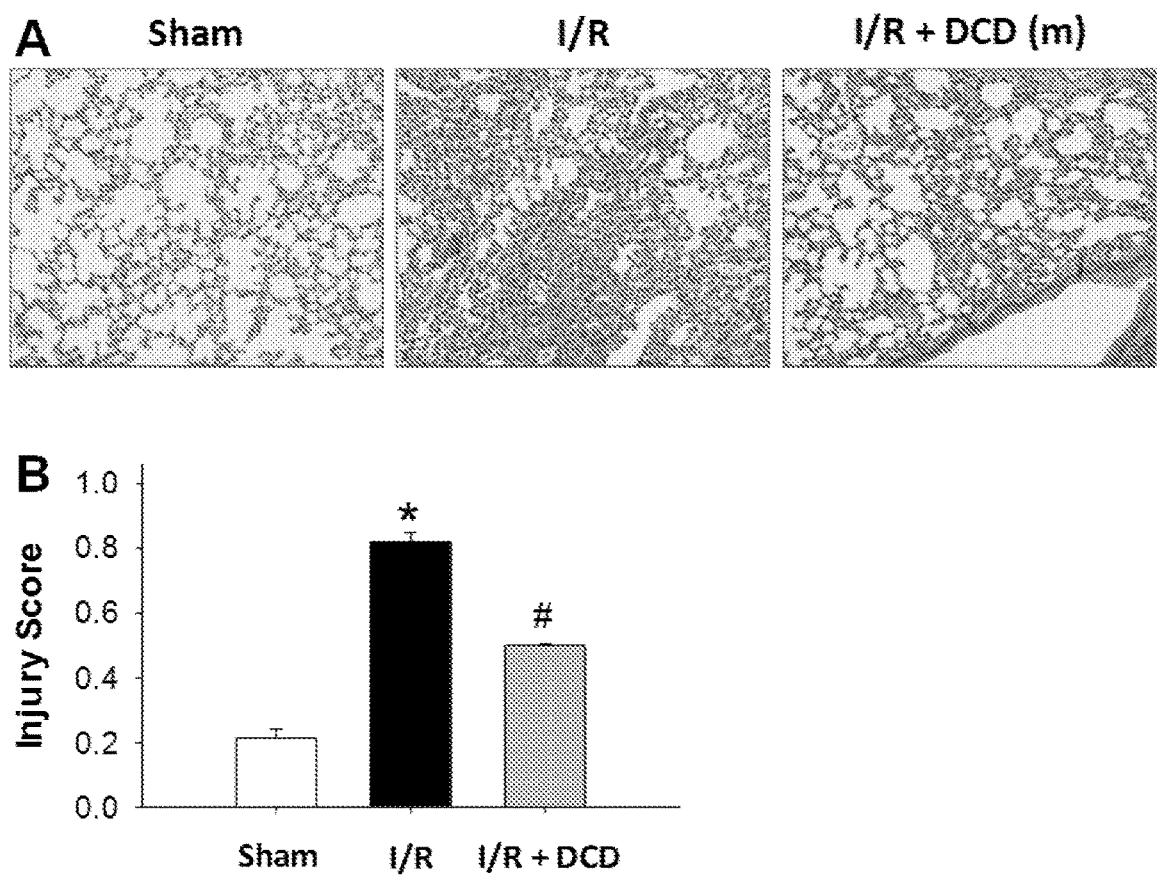
FIG. 6A-6B. DCD protects against hepatic ischemic/reperfusion-induced lung injury. 6A). Histopathological characteristics of lung injury after hepatic I/R. Representative H&E histological images of lung sections at 24 h post the onset of reperfusion. Note a normal lung architecture in the "Sham" control, and extensive lung injury and neutrophil infiltration in the "I/R" group. DCD treatment group ("I/R+DCD") exhibited a well-preserved tissue structure. 6B). Histological Scores. Lung injury was assessed histologically using American Thoracic Society Documents' lung injury scores, and expressed as means±S.E. of 3-6 animals per group. *P<0.05 vs. sham; #P<0.05 vs. "I/R" group.

DCD also protects against hepatic ischemic/reperfusion-induced lung injury. FIG. 6 shows histopathological characteristics of lung injury after hepatic I/R. In FIG. 6A are shown representative H&E histological images of lung sections at 24 h post the onset of reperfusion. Note a normal lung architecture in the "Sham" control, and extensive lung injury and neutrophil infiltration in the "I/R" group. DCD treatment group ("I/R+DCD") exhibited a well-preserved tissue structure. FIG. 6B shows histological Scores. Lung injury was assessed histologically using American Thoracic Society Documents' lung injury scores, and expressed as means±S.E. of 3-6 animals per group. *P<0.05 vs. sham; #P<0.05 vs. "I/R" group.

Figure 7:
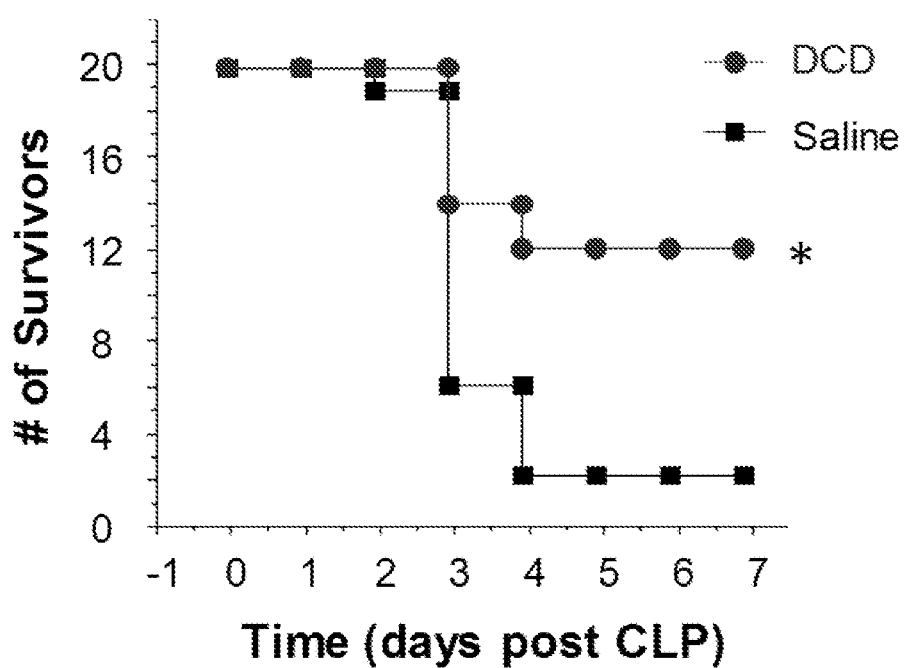
FIG. 7. DCD protects against lethal sepsis in mice. Balb/C mice (7-10 weeks, 20-25 g, male) were subjected to sepsis by cecal ligation and puncture as previously described. Briefly, Balb/c mice were anesthetized with Ketamine (75 mg/kg, intramuscularly) and xylazine (10 mg/kg, intramuscularly) before a 15 mm midline incision was made to expose the cecum. A 4-0 Prolene suture ligature was placed at a level 5.0 mm from the cecal tip away from the ileocecal valve, and the ligated cecal stump was then punctured once with a 22-gauge needle without direct extrusion of stool. The cecum was then replaced back into its normal intra-abdominal position, and the abdomen wound was closed with staples (wound clips) to prevent leakage of fluid. All animals were resuscitated with a normal saline solution (subcutaneously at 20 ml/kg of body weight), and given a subcutaneous injection of imipenem (0.5 mg/mouse in 200 µl sterile saline) (Primaxin, Merck & Co., Inc., West Point, Pa.) 30 minutes after the surgery. Saline or recombinant DCD (0.2 mg/kg body weight) were given intraperitoneally at +2 and +24 h post CLP surgery, and animal survival rates were monitored for up to two weeks. The Kaplan-Meier method was used to compare the differences in mortality rates between groups. Shown in the figure was a summary of two independent experiments with similar results. *, P<0.05 versus saline control group.

DCD was also found to protect against lethal sepsis in mice. Balb/C mice (7-10 weeks, 20-25 g, male) were subjected to sepsis by cecal ligation and puncture as previously described. Briefly, Balb/c mice were anesthetized with Ketamine (75 mg/kg, intramuscularly) and xylazine (10 mg/kg, intramuscularly) before a 15 mm midline incision was made to expose the cecum. A 4-0 Prolene suture ligature was placed at a level 5.0 mm from the cecal tip away from the ileocecal valve, and the ligated cecal stump was then punctured once with a 22-gauge needle without direct extrusion of stool. The cecum was then replaced back into its normal intra-abdominal position, and the abdomen wound was closed with staples (wound clips) to prevent leakage of fluid. All animals were resuscitated with a normal saline solution (subcutaneously at 20 ml/kg of body weight), and given a subcutaneous injection of imipenem (0.5 mg/mouse in 200 μl sterile saline) (Primaxin, Merck & Co., Inc., West Point, Pa.) 30 minutes after the surgery. Saline or recombinant DCD (0.2 mg/kg body weight) were given intraperitoneally at +2 and +24 h post CLP surgery, and animal survival rates were monitored for up to two weeks. The Kaplan-Meier method was used to compare the differences in mortality rates between groups. Shown in FIG. 7 is a summary of two independent experiments with similar results. *, P<0.05 versus saline control group.

Materials and Methods

Materials: Bacterial endotoxin (lipopolysaccharide, LPS, *E. coli* 0111:B4, Cat. No. L4130) was obtained from Sigma-Aldrich (St. Louis, Mo.). Dulbecco's Modified Eagle's Medium (DMEM, Cat. No. 11995-065), penicillin/streptomycin (Cat. No. 15140-122) and fetal bovine serum (FBS, Cat. No. 26140079) were from Invitrogen (Grand Island, N.Y.). Recombinant HMGB1 and CIRP were expressed in *E. coli*, and purified to remove contaminating endotoxin by Triton X-114 extraction as previously described (10, 19). To express recombinant dermcidin, the cDNA encoding for the mature form of dermcidin (DCD, NM_053283.2) (corresponding to residues 20-110, without the N-terminal signal peptide, amino acid 1-19) was cloned onto a pReceiver-B01 (CS-T3198-B01-01, GeneCopoeia) vector, and the recombinant DCD was expressed in *E. coli* BL21 (DE3) pLysS cells. Recombinant DCD containing an N-terminal histidine tag (His-DCD) was isolated and purified to remove contaminating endotoxin by Triton X-114 extraction.

Cell culture: Murine macrophage-like RAW 264.7 were obtained from the American Type Culture Collection (ATCC, Rockville, Md.), and were cultured in DMEM supplemented with 1% penicillin/streptomycin and 10% FBS. Human blood was purchased from the Long Island Blood Bank (Melville, N.Y.), and human peripheral blood mononuclear cells (HuPBMCs) were isolated by density gradient centrifugation through Ficoll (Ficoll-Paque PLUS, Pharmacia, Piscataway, N.J.) as previously described (20-22). Adherent macrophages or HuPBMCs were gently washed with, and cultured in, DMEM before stimulation with LPS (0.4 µg/ml), CIRP (2.0 µg/ml), or HMGB1 (1.0 µg/ml) in the absence or presence of recombinant dermcidin for 16 h. Subsequently, the cell-conditioned culture media were analyzed respectively for levels of nitric oxide, and other cytokines by the Griess Reaction and Cytokine Antibodies Arrays as previously described (19, 23).

Nitric oxide (NO) assay: The levels of NO in the culture medium were determined indirectly by measuring the $NO^{2-}$ production with a colorimetric assay based on the Griess reaction (21, 24). $NO^{2-}$ concentrations were determined with reference to a standard curve generated with sodium nitrite at various dilutions.

Cytokine antibody array: Human Cytokine Antibody Array C3 (Cat. No. AAH-CYT-3-4, RayBiotech Inc., Norcross, Ga., USA), which respectively detect 42 cytokines on one membrane, were used to determine cytokine levels in human monocyte-conditioned culture medium as previously described (21, 24). Briefly, the membranes were sequentially incubated with equal volumes of cell culture medium (200 al), primary biotin-conjugated antibodies, and horseradish peroxidase-conjugated streptavidin. After exposing to X-ray film, the relative signal intensity was determined using the Scion Image software.

Statistical analysis: Data are expressed as mean±SEM of two independent experiments in triplicates. One-way analyses of variance (ANOVA) followed by the Tukey's test for multiple comparisons were used to compare between different groups. A P value less than 0.05 was considered statistically significant.

REFERENCES

1. Schittek B, Hipfel R, Sauer B, Bauer J, Kalbacher H, Stevanovic S, Schirle M, Schroeder K, Blin N, Meier F, et al.: a novel human antibiotic peptide secreted by sweat glands. *Nat Immunol* 2(12): 1133-1137, 2001.
2. Li M, Rigby K, Lai Y, Nair V, Peschel A, Schittek B, Otto M: *Staphylococcus aureus* mutant screen reveals interaction of the human antimicrobial peptide dermcidin with membrane phospholipids. *Antimicrob Agents Chemother* 53(10):4200-4210, 2009.
3. Lai Y, Villaruz A E, Li M, Cha D J, Sturdevant D E, Otto M: The human anionic antimicrobial peptide dermcidin induces proteolytic defence mechanisms in staphylococci. *Mol Microbiol* 63(2):497-506, 2007.
4. Steffen H, Rieg S, Wiedemann I, Kalbacher H, Deeg M, Sahl H G, Peschel A, Gotz F, Garbe C, Schittek B. Naturally processed dermcidin-derived peptides do not permeabilize bacterial membranes and kill microorganisms irrespective of their charge. *Antimicrob Agents Chemother* 50(8):2608-2620, 2006.
5. Rieg S, Seeber S, Steffen H, Humeny A, Kalbacher H, Stevanovic S, Kimura A, Garbe C, Schittek B: Generation of multiple stable dermcidin-derived antimicrobial peptides in sweat of different body sites. *J Invest Dermatol* 126(2):354-365, 2006.
6. Wang H, Zhu S, Zhou R, Li W, Sama A E: Therapeutic potential of HMGB1-targeting agents in sepsis. *Expert Rev Mol Med* 10:e32, 2008.
7. Salomao R, Martins P S, Brunialti M K, Femandes M L, Martos L S, Mendes M E, Gomes N E, Rigato O. TLR signaling pathway in patients with sepsis. *Shock* 30 Suppl 1:73-77, 2008.
8. Akira S, Takeda K: Toll-like receptor signalling. *Nat Rev Immunol* 4(7):499-511, 2004.
9. Wang H, Bloom O, Zhang M, Vishnubhakat J M, Ombrellino M, Che J, Frazier A, Yang H, Ivanova S, Borovikova L, et al.: HMG-1 as a late mediator of endotoxin lethality in mice. *Science* 285(5425):248-251, 1999.
10. Qiang X, Yang W L, Wu R, Zhou M, Jacob A, Dong W, Kuncewitch M, Ji Y, Yang H, Wang H, et al.: Cold-inducible RNA-binding protein (CIRP) triggers inflammatory responses in hemorrhagic shock and sepsis. *Nat Med* 19(11):1489-1495, 2013.
11. Godwin A, Yang W L, Sharma A, Khader A, Wang Z, Zhang F, Nicastro J, Coppa G F, Wang P. Blocking cold-inducible RNA-binding protein protects liver from ischemia-reperfusion injury. *Shock* 43(1):24-30, 2015.
12. MacMicking J D, Nathan C, Hom G, Chartrain N, Fletcher D S, Trumbauer M, Stevens K, Xie Q W, Sokol K, Hutchinson N: Altered responses to bacterial infection and endotoxic shock in mice lacking inducible nitric oxide synthase. *Cell* 81(4):641-650, 1995.
13. Scaffidi P, Misteli T, Bianchi M E: Release of chromatin protein HMGB1 by necrotic cells triggers inflammation. *Nature* 418(6894):191-195, 2002.
14. Tsung A, Sahai R, Tanaka H, Nakao A, Fink M P, Lotze M T, Yang H, Li J, Tracey K J, Geller D A, et al.: The nuclear factor HMGB1 mediates hepatic injury after murine liver ischemia-reperfusion. *J Exp Med* 201(7):1135-1143, 2005.
15. Peltz E D, Moore E E, Eckels P C, Damle S S, Tsuruta Y, Johnson J L, Sauaia A, Silliman C C, Banerjee A, Abraham E: HMGB1 is markedly elevated within 6 hours of mechanical trauma in humans. *Shock* 32(1):17-22, 2009.
16. Antoine D J, Dear J W, Lewis P S, Platt V, Coyle J, Masson M, Thanacoody R H, Gray A J, Webb D J, Moggs J G, et al.: Mechanistic biomarkers provide early and sensitive detection of acetaminophen-induced acute liver injury at first presentation to hospital. *Hepatology* 58(2):777-787, 2013.
17. Andersson U, Tracey K J: HMGB1 is a therapeutic target for sterile inflammation and infection. *Annu Rev Immunol* 29:139-62, 2011.
18. Petros A, Lamb G, Leone A, Moncada S, Bennett D, Vallance P: Effects of a nitric oxide synthase inhibitor in humans with septic shock. *Cardiovasc Res* 28(1):34-39, 1994.

19. Zhu S, Ashok M, Li J, Li W, Yang H, Wang P, Tracey K J, Sama A E, Wang H: Spermine protects mice against lethal sepsis partly by attenuating surrogate inflammatory markers. *Mol Med* 15(7-8):275-282, 2009.
20. Chen G, Li J, Ochani M, Rendon-Mitchell B, Qiang X, Susarla S, Ulloa L, Yang H, Fan S, Goyert S M, et al.: Bacterial endotoxin stimulates macrophages to release HMGB1 partly through CD14- and TNF-dependent mechanisms. *J Leukoc Biol* 76(5):994-1001, 2004.
21. Li W, Li J, Ashok M, Wu R, Chen D, Yang L, Yang H, Tracey K J, Wang P, Sama A E, et al.: A cardiovascular drug rescues mice from lethal sepsis by selectively attenuating a late-acting proinflammatory mediator, high mobility group box 1. *J Immunol* 178(6):3856-3864, 2007.
22. Rendon-Mitchell B, Ochani M, Li J, Han J, Wang H, Yang H, Susarla S, Czura C, Mitchell R A, Chen G, et al.: IFN-gamma Induces High Mobility Group Box 1 Protein Release Partly Through a TNF-Dependent Mechanism. *J Immunol* 170(7):3890-3897, 2003.
23. Li W, Li J, Sama A E, Wang H: Carbenoxolone Blocks Endotoxin-Induced Protein Kinase R (PKR) Activation and High Mobility Group Box 1 (HMGB1) Release. *Mol Med* 19(1):203-211, 2013.
24. Li W, Ashok M, Li J, Yang H, Sama A E, Wang H: A Major Ingredient of Green Tea Rescues Mice from Lethal Sepsis Partly by Inhibiting HMGB1. *PLoS ONE* 2(11): e1153, 2007.
25. Stewart G D, Lowrie A G, Riddick A C, Fearon K C, Habib F K, Ross J A. Dermcidin expression confers a survival advantage in prostate cancer cells subjected to oxidative stress or hypoxia. *Prostate* 67(12): 1308-1317, 2007
26. Porter D, Weremowicz S, Chin K, Seth P, Keshaviah A, Lahti-Domenici J, Bae Y K, Monitto C L, Merlos-Suarez A, Chan J, Hulette C M, Richardson A, Morton C C, Marks J, Duyao M, Hruban R, Gabrielson E, Gelman R, Polyak K. A neural survival factor is a candidate oncogene in breast cancer. *Proc Natl Acad Sci USA* 100(19):10931-10936, 2003.
27. Schittek B. The multiple facets of dermcidin in cell survival and host defense. *J Innate Immun* 4(4):349-360, 2012.
28. Pathak S, De Souza G A, Salte T, Wiker H G, Asjo B. HIV induces both a down-regulation of IRAK-4 that impairs TLR signalling and an up-regulation of the antibiotic peptide dermcidin in monocytic cells. *Scand J Immunol* 70(3):264-276, 2009.
29. Nakano T, Yoshino T, Fujimura T, Arai S, Mukuno A, Sato N, Katsuoka K. Reduced Expression of Dermcidin, a Peptide Active Against *Propionibacterium acnes*, in Sweat of Patients with Acne Vulgaris. *Acta Derm Venereol* 95(7):783-986, 2015.
30. Niyonsaba F, Suzuki A, Ushio H, Nagaoka I, Ogawa H, Okumura K. The human antimicrobial peptide dermcidin activates normal human keratinocytes. *Br J Dermatol* 160(2):243-249, 2009.
31. Wichterman K A, Baue A E, Chaudry I H: Sepsis and septic shock—a review of laboratory models and a proposal. *J Surg Res* 29(2):189-201, 1980.
32. Eskandari M K, Bolgos G, Miller C, Nguyen D T, DeForge L E, Remick D G: Anti-tumor necrosis factor antibody therapy fails to prevent lethality after cecal ligation and puncture or endotoxemia. *J Immunol* 148(9): 2724-2730, 1992.
33. Sallusto F, Baggiolini M. Chemokines and leukocyte traffic. *Nat Immunol* 9(9):949-952, 2008.
34. Feldmann M, Maini R N. Anti-TNF alpha therapy of rheumatoid arthritis: what have we learned? *Annu Rev Immunol* 19:163-196, 2001.
35. Osuchowski M F, Remick D G, Lederer J A, Lang C H, Aasen A O, Aibiki M, Azevedo L C, Bahrami S, Boros M, Cooney R, et al.: Abandon the mouse research ship? Not just yet! *Shock* 41(6):463-475, 2014.

What is claimed is:

1. A method of inhibiting sterile organ transplantation-associated ischemia/reperfusion and/or organ transplantation-associated inflammation in a recipient subject comprising storing and/or rinsing the organ to be transplanted in a solution comprising an amount of an isolated-dermcidin peptide having SEQ ID NO:1 wherein the cysteine at position 15 ("Cysteine 34") is optionally substituted with a serine and wherein SEQ ID NO:1 optionally has an N-terminal histidine tag, effective to inhibit sterile organ transplantation-associated ischemia/reperfusion and/or organ transplantation-associated inflammation in a recipient subject.

2. The method of claim 1, wherein the organ is a kidney, liver, heart, or lung.

* * * * *

UNITED STATES PATENT AND TRADEMARK OFFICE
CERTIFICATE OF CORRECTION

| | |
|---|---|
| PATENT NO. | : 11,266,716 B2 |
| APPLICATION NO. | : 15/769880 |
| DATED | : March 8, 2022 |
| INVENTOR(S) | : Ping Wang and Haichao Wang |

It is certified that error appears in the above-identified patent and that said Letters Patent is hereby corrected as shown below:

In the Specification

In Column 1, Line 18, please change "GM076179" to --HL076179--.

Signed and Sealed this
Fifth Day of July, 2022

Katherine Kelly Vidal
*Director of the United States Patent and Trademark Office*

SEQUENCE LISTING

```
<160> NUMBER OF SEQ ID NOS: 8

<210> SEQ ID NO 1
<211> LENGTH: 91
<212> TYPE: PRT
<213> ORGANISM: Homo sapiens

<400> SEQUENCE: 1

Tyr Asp Pro Glu Ala Ala Ser Ala Pro Gly Ser Gly Asn Pro Cys His
1               5                   10                  15

Glu Ala Ser Ala Ala Gln Lys Glu Asn Ala Gly Glu Asp Pro Gly Leu
            20                  25                  30

Ala Arg Gln Ala Pro Lys Pro Arg Lys Gln Arg Ser Ser Leu Leu Glu
        35                  40                  45

Lys Gly Leu Asp Gly Ala Lys Lys Ala Val Gly Gly Leu Gly Lys Leu
    50                  55                  60

Gly Lys Asp Ala Val Glu Asp Leu Glu Ser Val Gly Lys Gly Ala Val
65                  70                  75                  80

His Asp Val Lys Asp Val Leu Asp Ser Val Leu
                85                  90

<210> SEQ ID NO 2
<211> LENGTH: 17
<212> TYPE: PRT
```

<213> ORGANISM: Homo sapiens

<400> SEQUENCE: 2

Glu Ser Val Gly Lys Gly Ala Val His Asp Val Lys Asp Val Leu Asp
1               5                   10                  15

Ser

<210> SEQ ID NO 3
<211> LENGTH: 37
<212> TYPE: PRT
<213> ORGANISM: Homo sapiens

<400> SEQUENCE: 3

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
        35

<210> SEQ ID NO 4
<211> LENGTH: 24
<212> TYPE: PRT
<213> ORGANISM: Homo sapiens

<400> SEQUENCE: 4

Leu Glu Lys Gly Leu Asp Gly Ala Lys Lys Ala Val Gly Gly Leu Gly
1               5                   10                  15

Lys Leu Gly Lys Asp Ala Val Glu
            20

<210> SEQ ID NO 5
<211> LENGTH: 29
<212> TYPE: PRT
<213> ORGANISM: Homo sapiens

<400> SEQUENCE: 5

Ser Ser Leu Leu Glu Lys Gly Leu Asp Gly Ala Lys Lys Ala Val Gly
1               5                   10                  15

Gly Leu Gly Lys Leu Gly Lys Asp Ala Val Glu Asp Leu
            20                  25

<210> SEQ ID NO 6
<211> LENGTH: 25
<212> TYPE: PRT
<213> ORGANISM: Homo sapiens

<400> SEQUENCE: 6

Ser Ser Leu Leu Glu Lys Gly Leu Asp Gly Ala Lys Lys Ala Val Gly
1               5                   10                  15

Gly Leu Gly Lys Leu Gly Lys Asp Ala
            20                  25

<210> SEQ ID NO 7
<211> LENGTH: 48
<212> TYPE: PRT
<213> ORGANISM: HOMO SAPIENS

<400> SEQUENCE: 7

Ser Ser Leu Leu Glu Lys Gly Leu Asp Gly Ala Lys Lys Ala Val Gly
1               5                   10                  15

```
Gly Leu Gly Lys Leu Gly Lys Asp Ala Val Glu Asp Leu Glu Ser Val
            20                  25                  30

Gly Lys Gly Ala Val His Asp Val Lys Asp Val Leu Asp Ser Val Leu
            35                  40                  45

<210> SEQ ID NO 8
<211> LENGTH: 47
<212> TYPE: PRT
<213> ORGANISM: HOMO SAPIENS

<400> SEQUENCE: 8

Ser Ser Leu Leu Glu Lys Gly Leu Asp Gly Ala Lys Lys Ala Val Gly
1               5                   10                  15

Gly Leu Gly Lys Leu Gly Lys Asp Ala Val Glu Asp Leu Glu Ser Val
            20                  25                  30

Gly Lys Gly Ala Val His Asp Val Lys Asp Val Leu Asp Ser Val
            35                  40                  45
```